(12) United States Patent
Yamamoto et al.

(10) Patent No.: US 8,403,018 B2
(45) Date of Patent: Mar. 26, 2013

(54) MANUFACTURING EQUIPMENT OF WEARING ARTICLE

(75) Inventors: Hiroki Yamamoto, Kagawa (JP); Kenji Takeuchi, Kagawa (JP); Fumihito Kawazu, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 271 days.

(21) Appl. No.: 12/672,431

(22) PCT Filed: Jul. 24, 2008

(86) PCT No.: PCT/JP2008/063232
§ 371 (c)(1),
(2), (4) Date: Mar. 25, 2010

(87) PCT Pub. No.: WO2009/022530
PCT Pub. Date: Feb. 19, 2009

(65) Prior Publication Data
US 2011/0114264 A1  May 19, 2011

(30) Foreign Application Priority Data
Aug. 10, 2007 (JP) ................. 2007-210110

(51) Int. Cl.
*B32B 37/00* (2006.01)
*B32B 37/02* (2006.01)
*B32B 38/00* (2006.01)
*B32B 38/04* (2006.01)

(52) U.S. Cl. ........ 156/516; 156/349; 156/367; 156/381; 156/443; 156/510

(58) Field of Classification Search .................. 156/349, 156/367, 381, 443, 510, 516
See application file for complete search history.

(56) References Cited

U.S. PATENT DOCUMENTS
4,938,753 A * 7/1990 Van Gompel et al. ... 604/385.29
(Continued)

FOREIGN PATENT DOCUMENTS
EP 0589859 B1 3/1994
EP 1569587 10/2007
(Continued)

OTHER PUBLICATIONS
Egyptian Office Action dated Sep. 2, 2010.
(Continued)

*Primary Examiner* — Mark A Osele
*Assistant Examiner* — Christopher C Caillouet
(74) *Attorney, Agent, or Firm* — Lowe Hauptman Ham & Berner, LLP (57) ABSTRACT

Equipment of manufacturing a wearing article includes a plurality of units movably arranged on a unit basis for transferring a half-completed product of the wearing article. The plurality of units is configured to perform the steps of shaping pulverized pulp into an absorbent body, sandwiching the absorbent body between first and second sheet members to obtain a continuous body of an absorbent main body, producing at least apart of a belt element, severing the continuous body to obtain the absorbent main body, affixing a pair of the belt elements to end sections of the absorbent main body, folding the absorbent main body in two, and superposing the belt elements on each other, joining the superposing belt elements at intervals at a to-be-joined portion to obtain the waist-belt section, and severing the continuous body corresponding to the to-be-joined portion for each waist-belt section to obtain the wearing article.

10 Claims, 7 Drawing Sheets

U.S. PATENT DOCUMENTS

| | | | |
|---|---|---|---|
| 5,237,736 | A | 8/1993 | Inoue et al. |
| 5,492,591 | A | 2/1996 | Herrmann et al. |
| 6,273,165 | B1 | 8/2001 | Gundersen et al. |
| 6,574,520 | B1 * | 6/2003 | Liu et al. .................... 700/96 |
| 2002/0193972 | A1 | 12/2002 | Kudo et al. |
| 2003/0004594 | A1 | 1/2003 | Liu et al. |

FOREIGN PATENT DOCUMENTS

| | | |
|---|---|---|
| JP | 10-052456 A | 2/1998 |
| JP | 10505246 | 5/1998 |
| JP | 2002-370142 A | 12/2002 |
| JP | 2003-062739 A | 3/2003 |
| JP | 2003521771 | 7/2003 |
| JP | 2004-268204 A | 9/2004 |
| JP | 2004-329238 A | 11/2004 |
| JP | 2006507891 | 3/2006 |
| JP | 2006-101970 A | 4/2006 |
| JP | 2007-105453 A | 4/2007 |

OTHER PUBLICATIONS

Eurasian Office Action 201000304/31 issued on Aug. 3, 2011.
Eurasian Office Action, issued Feb. 8, 2011.
PCT/JP2008/063232 International Search Report.
Office Action for EA201000304, dated Mar. 7, 2012.
Japanese Office Action for Application No. 2007-210110 mailed Jul. 17, 2012.
Extended European Search Report corresponding to EP 08791484.2, dated Sep. 25, 2012.
Office Action corresponding to AU 2008287991, dated Sep. 13, 2012.

* cited by examiner

MANUFACTURING EQUIPMENT OF WEARING ARTICLE

RELATED APPLICATIONS

The present application is based on International Application PCT/JP2008/063232, filed Jul. 24, 2008, which claims priority from Japan Application Number 2007-210110, filed Aug. 10, 2007, the disclosures of which are hereby incorporated by reference herein in their entirety.

TECHNICAL FIELD

The invention relates to manufacturing equipments of wearing articles such as disposable diapers.

BACKGROUND ART

A so-called disposable diaper (hereinafter referred to as a diaper) have conventionally been known as an example of a wearing article including an absorbent main body that has an absorbent body absorbing fluid and is applied to a crotch and a waist-belt section covering waist around (see JP-A-2006-101970).

DISCLOSURE OF INVENTION

Problem to be Solved by the Invention

The diaper is produced from raw material to finished product in its production line, for example, using nonwoven fabrics, etc. as a material. This production line has generally a belt conveyor arranged therein. A half-completed diaper moves on the belt conveyor while being supported by the belt conveyor, and devices of stations combine the half-completed diaper and various constituent parts such as an absorbent body made of pulverized pulp, etc. or a sheet member covering the absorbent body and complete the diaper as a final product.

When constructing the above-mentioned production line from raw material to finished product, first, various devices necessary for the production line are manufactured in a dedicated machine factory of a machine manufacturer. These devices are assembled in the factory to finish a manufacturing equipment of a diaper; then, a test-run is giving to the manufacturing equipment to verify whether imperfection exists. Thereafter, the manufacturing equipment of the diaper is disassembled, accommodated in a container, transported to a factory place in the destination, and is installed on a foundation, etc. of the factory place in sequence.

However, a size of a container is standardized under the JIS or ISO standard. Therefore, in disassembly after the above-mentioned test-run, it is necessary to disassemble the manufacturing equipment into a size as small as a container can accommodate them. There are cases in which if a device such as a belt conveyor cannot be accommodated on a device basis, it is necessary to further disassemble the device. In such a case, the construction time will become longer because it takes a long time for re-assembly in the factory place.

The invention has been made in view of the conventional problems described above, and an advantage thereof is to provide a manufacturing equipment of a wearing article such as a disposable diaper, the manufacturing equipment being capable of the reduction of a construction time for the manufacturing equipment of the wearing article.

Means for Solving the Problem

In order to achieve the above-described advantages, a principal aspect of the invention is a manufacturing equipment of a wearing article including an absorbent main body and a waist-belt section, the absorbent main body having an absorbent body that absorbs fluid and being applied to a crotch, the waist-belt section covering a waist around, including:
  a plurality of units
  that are movably arranged on a unit basis,
    between which a half-completed product of the wearing article is transferred along a certain first direction,
  that respectively have a planar size in which a length in a second direction perpendicular to the first direction is longer than in the first direction,
  whose respective height and lengths of the first direction and the second direction are within a size range so that the units can be respectively accommodated in a container according to the JIS or ISO standard, and
  that respectively perform at least one of
    a step in which pulverized pulp is shaped into the absorbent body,
    a step in which the absorbent body is sandwiched between a first sheet member and a second sheet member, and a continuous body of the absorbent main body is formed,
    a step in which at least a part of a belt element constituting the waist-belt section is produced,
    a step in which the continuous body of the absorbent main body is severed, and the absorbent main body is produced,
    a step in which a pair of the belt elements are affixed to both end sections of the absorbent main body,
    a step in which the absorbent main body is folded in two, and the pair of belt elements superpose,
    a step in which the superposing belt elements are joined at intervals at a to-be-joined portion, and the waist-belt section is produced, and
    a step in which severing is performed corresponding to the to-be-joined portion for each waist-belt section, and the wearing article is formed.

Features of the invention other than the above will become clear by reading the description of the present specification with reference to the accompanying drawings.

Effects of the Invention

With the invention, it is possible to reduce a construction time for a manufacturing equipment of a wearing article such as a disposable diaper.

BRIEF DESCRIPTION OF DRAWINGS

FIG. 3 FIG. 3A is a cross-sectional view taken along III-III in FIG. 2.

FIG. 5 FIGS. 5A and 5B are layouts of a manufacturing equipment 30 of the diaper 1.

FIG. 6 FIGS. 6A to 6F are explanatory diagrams showing a producing process of a surface sheet member 12, etc. in an absorbent-body-shaping unit U2, and cross-sectional views showing the surface sheet member 12, etc., taken along a width direction.

FIG. 7 FIGS. 7A to 7J are explanatory diagrams showing a forming process of the absorbent main body 10, etc. in an absorbent-main-body-forming unit U3, and cross-sectional views showing the absorbent main body 10, etc. taken along a width direction (the same direction as a CD direction).

LIST REFERENCE NUMERALS 1 diaper (wearing article), 1a joined body, torso opening, 5 leg opening, 10 absorbent main body, 10a end section, 10b end section, 11 absorbent body, 12 surface sheet member (first sheet member), 13 tissue paper, 14 nonwoven fabric, 15 back face sheet member (second sheet member), 15p folding-line portion, 15s end section, 16 leakage-proof sheet, 17 nonwoven fabric, 18 rubber thread, 19 rubber thread, 20 waist-belt section, 23 belt element, 23s both end sections, 23m intermediate product, 24 nonwoven fabric (third sheet member), 25 belt element, 25s both end sections, 25m intermediate product, 26 rubber thread, 30 manufacturing equipment, 31 pulp sheet, 33 pulverizer, 39 pulp supplying duct, 41 turn roller, 42 layering drum, 47 guiding member, 48 pressing roller, 49 guide roller, 50 guide roller, 52a turn roller, 52b turn roller, 59 guide roller, 60 guide roller, 61 rotating drum (joining apparatus), 63 cutter roll, 64 pressure roller, 65c turn roller, 66 two-folding guiding member, 67 rotating drum (sealing apparatus), 72 slitter, 73a turn roller, 73b turn roller, 74 guiding member, 81 first heat sealing roller, 82 second heat sealing roller, 91 base plate, 92 base plate, 93 base plate, 94 base plate, 95 base plate, U1 pulverized-pulp producing unit, U2 absorbent-body shaping unit, U3 absorbent-main-body forming unit, U4 joining unit, U5 intermediate-product producing unit, G foundation, S gap, LC line center, Pb folding position, Pc folding position,

BEST MODE FOR CARRYING OUT THE INVENTION

At least the following matters will be made clear by the description in the present specification and the accompanying drawings.

A manufacturing equipment of a wearing article including an absorbent main body and a waist-belt section, the absorbent main body having an absorbent body that absorbs fluid and being applied to a crotch, the waist-belt section covering a waist around, including:
  a plurality of units
  that are movably arranged on a unit basis,
  between which a half-completed product of the wearing article is transferred along a certain first direction,
  that respectively have a planar size in which a length in a second direction perpendicular to the first direction is longer than in the first direction,
  whose respective height and lengths of the first direction and the second direction are within a size range so that the units can be respectively accommodated in a container according to the JIS or ISO standard, and
  that respectively perform at least one of
    a step in which pulverized pulp is shaped into the absorbent body,
    a step in which the absorbent body is sandwiched between a first sheet member and a second sheet member, and a continuous body of the absorbent main body is formed,
    a step in which at least a part of a belt element constituting the waist-belt section is produced,
    a step in which the continuous body of the absorbent main body is severed, and the absorbent main body is produced,
    a step in which a pair of the belt elements are affixed to both end sections of the absorbent main body,
    a step in which the absorbent main body is folded in two, and the pair of belt elements superpose,
    a step in which the superposing belt elements are joined at intervals at a to-be-joined portion, and the waist-belt section is produced, and
    a step in which severing is performed corresponding to the to-be-joined portion for each waist-belt section, and the wearing article is formed.

With this manufacturing equipment of a wearing article, the units respectively perform at least one of the above-mentioned eight processes that are necessary for manufacturing of the wearing article. The units also are movable on a unit basis, and are within the size range so that the units can be respectively accommodated in a container according to the JIS or ISO standard.

Accordingly, when the units are transported with the container, and are each set in a factory place in the destination, at least the processes to be performed by the units can be performed immediately without assembling devices in the units and performing the position adjustment. Therefore, it is possible to shorten a construction time for the manufacturing equipment of the wearing article. Besides, before being transported by the container, the units themselves can efficiently be assembled in a dedicated machine factory with dedicated tools and the like. Therefore, it is possible to shorten a total construction time for the manufacturing equipment of the wearing article.

Further, regarding the planar size of the units, the second direction perpendicular to the first direction along which the half-completed product of the wearing article is transferred between the units is longer than the first direction. Therefore, while securing wide spaces in the second direction for arranging devices, materials, and the like in the units, a total length of the manufacturing equipment of the wearing article can be shortened in the first direction in which the half-completed product of the wearing article is transferred between the units. As a result thereof, it is possible to increase the transferring accuracy of the half-completed product of the manufacturing equipment as a whole; thereby, the wearing article can be processed more accurately.

In such a manufacturing equipment of a wearing article, it is preferable that between at least one pair of the units among the plurality of units, the half-completed product of the wearing article is transferred by continuously extending the half-completed product between the pair of units and transporting the half-completed product.

With this manufacturing equipment of a wearing article, it is possible to reduce the accuracy requirement for the position adjustment between at least a pair of the units. This is for the following reason. When manufacturing the wearing article, the half-completed product is continuously extended between the units, and thereby the half-completed product is transferred between the units. Therefore, even if there is some mismatch of the position adjustment between these units, the mismatch is absorbed due to flexible deformation of the continuous half-completed product.

Besides, it is possible to omit a belt conveyor for transporting the half-completed product, so that the number of constituent devices of the manufacturing equipment of the wearing article can be reduced.

In such a manufacturing equipment of a wearing article, it is preferable that the manufacturing equipment further includes
  an absorbent-main-body-forming unit that joins the first sheet member on which a plurality of the absorbent bodies placed along a flow direction and the second sheet member continuous in the flow direction, and that forms the continuous body of the absorbent main body continuous in the flow direction, and a joining unit that joins the belt element constituting the waist-belt section and the absorbent main body, wherein the absorbent main body is in a state of a continuous body along the flow direction, and is extended from the absorbent-main-body-forming unit to the joining unit and transferred to the joining unit, and in the extended portion, a weight of the absorbent main body is supported by only tension of the absorbent main body.

With this manufacturing equipment of a wearing article, it is possible to reduce the accuracy requirement for the position adjustment between the absorbent-main-body-forming unit and the joining unit. This is for the following reason. When manufacturing the wearing article, the continuous body of the absorbent main body is extended between the units, and thereby the absorbent main body is transferred from the absorbent-main-body-forming unit to the joining unit. Therefore, even if there is some mismatch of the position adjustment between these units, the mismatch is absorbed due to flexible deformation of the continuous body of the absorbent main body.

Besides, it is possible to omit a belt conveyor for transporting the absorbent main body, so that the number of constituent devices of the manufacturing equipment of the wearing article can be reduced.

In such a manufacturing equipment of a wearing article, it is preferable that the manufacturing equipment further includes an absorbent-body-shaping unit that shapes the pulverized pulp into the absorbent body, and places the absorbent body at a certain pitch in the flow direction on the first sheet member continuous in the flow direction, wherein the first sheet member on which the absorbent body is placed is extended from the absorbent-body-shaping unit to the absorbent-main-body-forming unit and transferred to the absorbent-main-body-forming unit, and in the extended portion, weights of the absorbent body and the first sheet member are supported by only tension of the first sheet member.

With this manufacturing equipment of a wearing article, it is possible to reduce the accuracy requirement for the position adjustment between the absorbent-body-shaping unit and the absorbent-main-body-forming unit. This is for the following reason. When manufacturing the wearing article, the first sheet member is extended between the units, and thereby the absorbent body is transferred together with the first sheet member from the absorbent-body-shaping unit to the absorbent-main-body-forming unit. Therefore, even if there is some mismatch of the position adjustment between these units, the mismatch is absorbed due to flexible deformation of the first sheet member.

Besides, it is possible to omit a belt conveyor for transporting the first sheet member on which the absorbent body is placed, so that the number of constituent devices of the manufacturing equipment of the wearing article can be reduced.

In such a manufacturing equipment of a wearing article, it is preferable that the manufacturing equipment further includes a pulverized-pulp-producing unit that pulverizes a sheet-like pulp and produces the pulverized pulp, wherein the pulverized pulp is supplied to the absorbent-body-shaping unit.

With this manufacturing equipment of a wearing article, since a sheet-like pulp can be delivered as a material, excellent handling of materials is achieved.

In such a manufacturing equipment of a wearing article, it is preferable that the manufacturing equipment further includes an intermediate-product-producing unit that produces an intermediate product of the belt element based on a third sheet member, wherein the intermediate product is in a state of a continuous body along the flow direction, and is extended from the intermediate-product-producing unit to the joining unit and transferred to the joining unit, in the extended portion, a weight of the intermediate product is supported by only tension of the intermediate product, and in the joining unit, the belt element is produced from the intermediate product.

With this manufacturing equipment of a wearing article, it is possible to reduce the accuracy requirement for the position adjustment between the intermediate-product-producing unit and the joining unit. This is for the following reason. When manufacturing the wearing article, the continuous body of the intermediate product is extended between the units, and thereby the intermediate product is transferred the intermediate-product-producing unit to the joining unit. Therefore, even if there is some mismatch of the position adjustment between these units, the mismatch is absorbed due to flexible deformation of the continuous body of the intermediate product.

Besides, it is possible to omit a belt conveyor for transporting the intermediate product, so that the number of constituent devices of the manufacturing equipment of the wearing article can be reduced.

In such a manufacturing equipment of a wearing article, in the joining unit, the both end sections of the absorbent main body may each be joined to one belt element, the absorbent main body being formed by severing the continuous body of the absorbent main body into a certain length in the flow direction.

In such a manufacturing equipment of a wearing article, it is preferable that the units have their respective base, and a constituent device of each of the units is fixed to and supported by the base corresponding to the unit of the constituent device.

With this manufacturing equipment of a wearing article, the units can be moved surely on a unit basis.

In such a manufacturing equipment of a wearing article, it is preferable that the base is a level plate member, the constituent device of each of the units is fixed on the plate member corresponding to the unit of the constituent device.

With this manufacturing equipment of a wearing article, since the base is the level plate member, it is easier to arrange constituent devices of the units.

Further, since it is possible to position lower the height of a processing position of each unit, the processing accuracy of the unit can be increased. The details are as follows. Generally, to increase the positioning accuracy of objects positioned in a low place is easier than in a high place. Here, the constituent device is directly placed and fixed on a top face of the above-mentioned plate member. Accordingly, the processing position (pass-line) of the constituent device can be positioned lower without using unnecessary legs, etc. at a portion positioned lower than the processing position (pass-line). As a result, it becomes possible to increase the processing accuracy of the constituent device.

Further, since a constituent device can be directly placed on a top face of the plate member, it is possible to prevent deterioration of the processing accuracy of the constituent device, the deterioration being likely to occur when the constituent device is supported by a so-called panel board. More specifically, in this panel board system, the panel board stands upright vertically and is provided on a foundation. The panel board supports the constituent device at one end of the device on a vertical plane of the panel board. However, in this system, a weight of the constituent device makes the panel board curve considerably, and it is difficult to maintain the positioning accuracy of the constituent device. As a result, the processing accuracy of the constituent device deteriorates. In this regard, if the constituent device is placed on the top face of the plate member, it is possible to inhibit deformation of the plate member, and to prevent deterioration of the processing accuracy of the constituent device by increasing the positioning accuracy of the constituent device.

In such a manufacturing equipment of a wearing article, it is preferable that among the units, units adjacent to each other are connected by a connecting member that is between bases of the adjacent units.

With this manufacturing equipment of a wearing article, it is possible to maintain in the long term positional relationship between the units after the position adjustment without installing and fixing each unit on a foundation of the factory place by an anchoring member such as an anchor bolt.

===Regarding Wearing Article 1===

Figure 1:
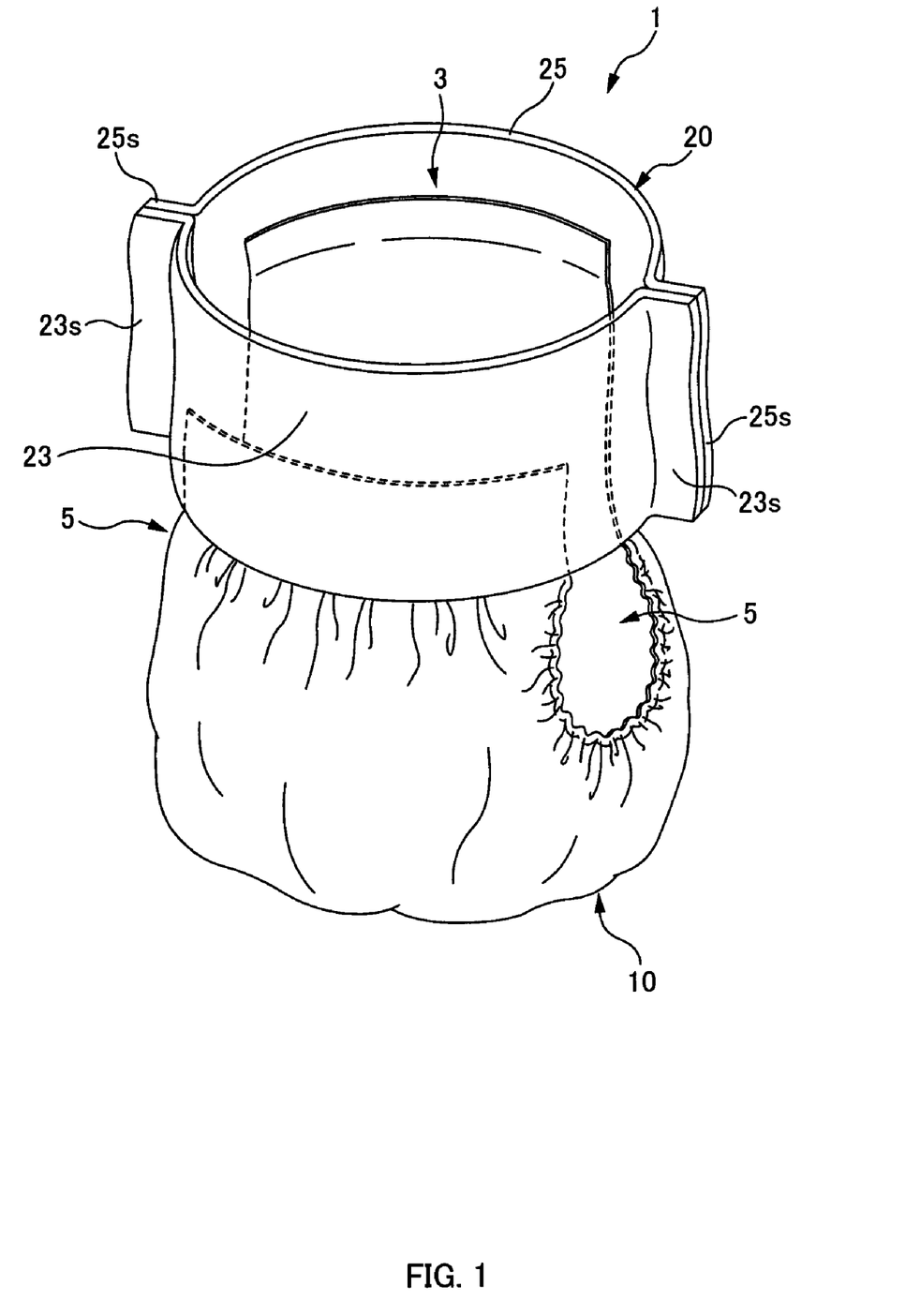
FIG. 1 This is a perspective view of a diaper 1 as a wearing article 1.

First, the configuration of a wearing article 1 manufactured with a manufacturing equipment 30 of the present embodiment is described. The wearing article 1 is a so-called diaper 1. FIG. 1 is a perspective view of the diaper 1. As shown in FIG. 1, the diaper 1 has a so-called pants shape on which a torso opening 3 and a pair of leg openings 5, 5 are formed; the diaper 1 includes an absorbent main body 10 that is applied to the crotch of a wearer, and a waist-belt section 20 for tie up the waist of the wearer with covering the waist around.

Figure 2:
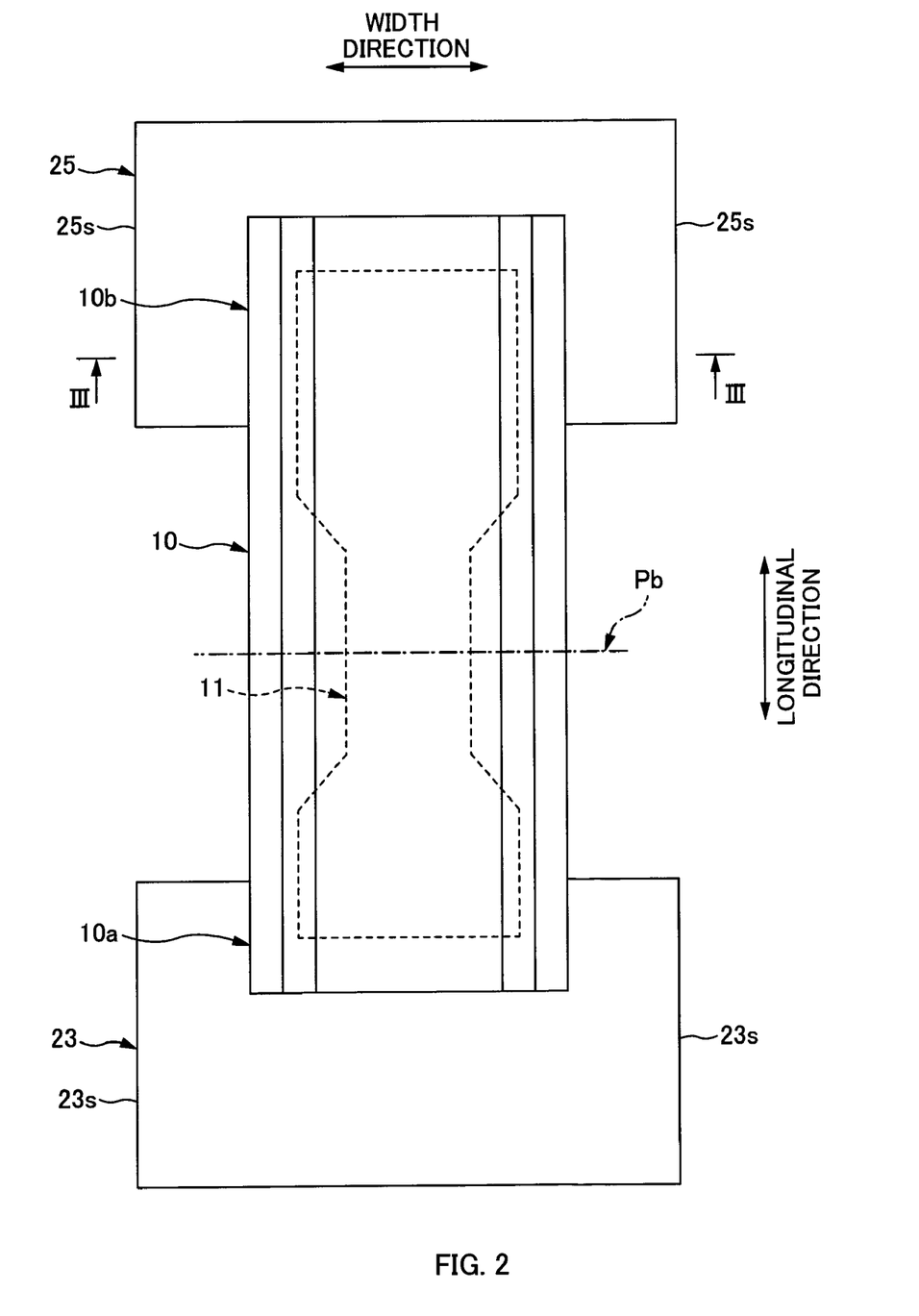
FIG. 2 This is a plan view showing a state in which the diaper 1 is opened flat.

FIG. 2 is a plan view showing a state in which the diaper 1 is opened flat by separating the waist-belt section 20, at a position where the waist-belt section 20 abuts the sides of a wearer, into a belt element 23 on a front face side and a belt element 25 on a back face side. In this opened state, the diaper 1 is formed with both end sections 10a, 10b of the absorbent main body 10 in a longitudinal direction adhering to a pair of the belt elements 23, 25 in such a manner as to extend between the pair of belt elements 23, 25 lined up in parallel having a certain space therebetween; an external shape of the diaper 1 is substantially H-shaped when viewed from above. Note that, the belt element 23, one of the belt elements, is a belt element on a front face side, and the belt element 25, the other of the belt elements, is a belt element on a back face side.

As well as the absorbent main body 10 is folded in two using its central section in the longitudinal direction as a folding position Pb, the belt elements 23, 25 opposing each other with the absorbent main body 10 being folded in two are welded and joined at both end sections 23s, 25s to be in contact with wearer's sides. Then, these belt elements 23, 25 are connected in a ring, to form the waist-belt section 20. Thereby, as shown in FIG. 1, while a torso opening 3 is formed, ends of the waist-belt section 20 and the absorbent main body 10 in a width direction forms the pair of leg openings 5, 5, to be in a shape of underpants.

Each of the constituent elements of the diaper 1 is described below.

<<<Absorbent Main Body 10>>>

Figure 3A:
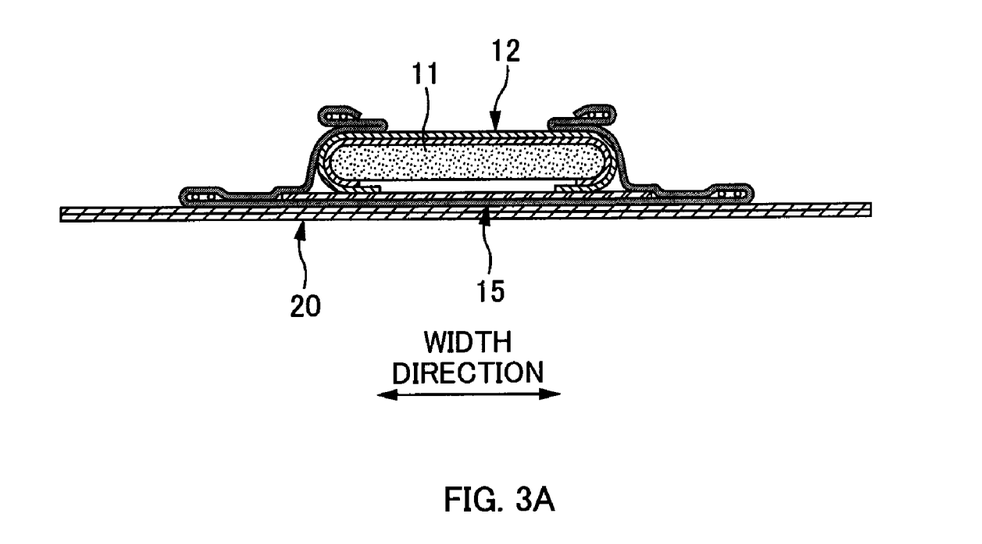
Figure 3B:
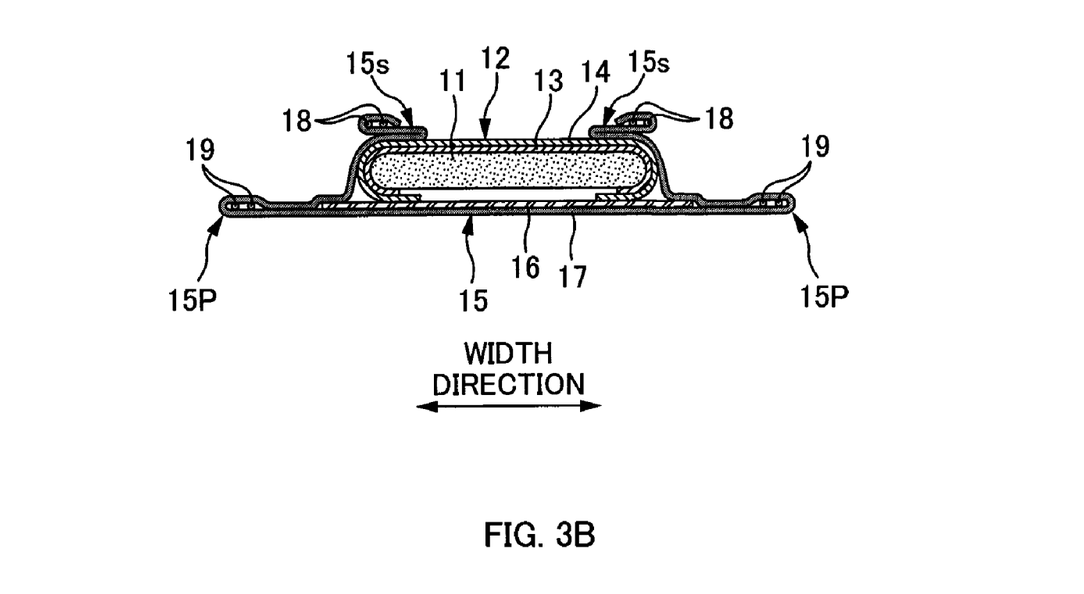
FIG. 3B is a cross-sectional view taken along III-III in FIG. 3A, showing only an absorbent main body 10.

FIG. 3A is a cross-sectional view taken along in FIG. 2. FIG. 3B is a cross-sectional view taken along in FIG. 3A, showing only the absorbent main body 10.

Figure 4:
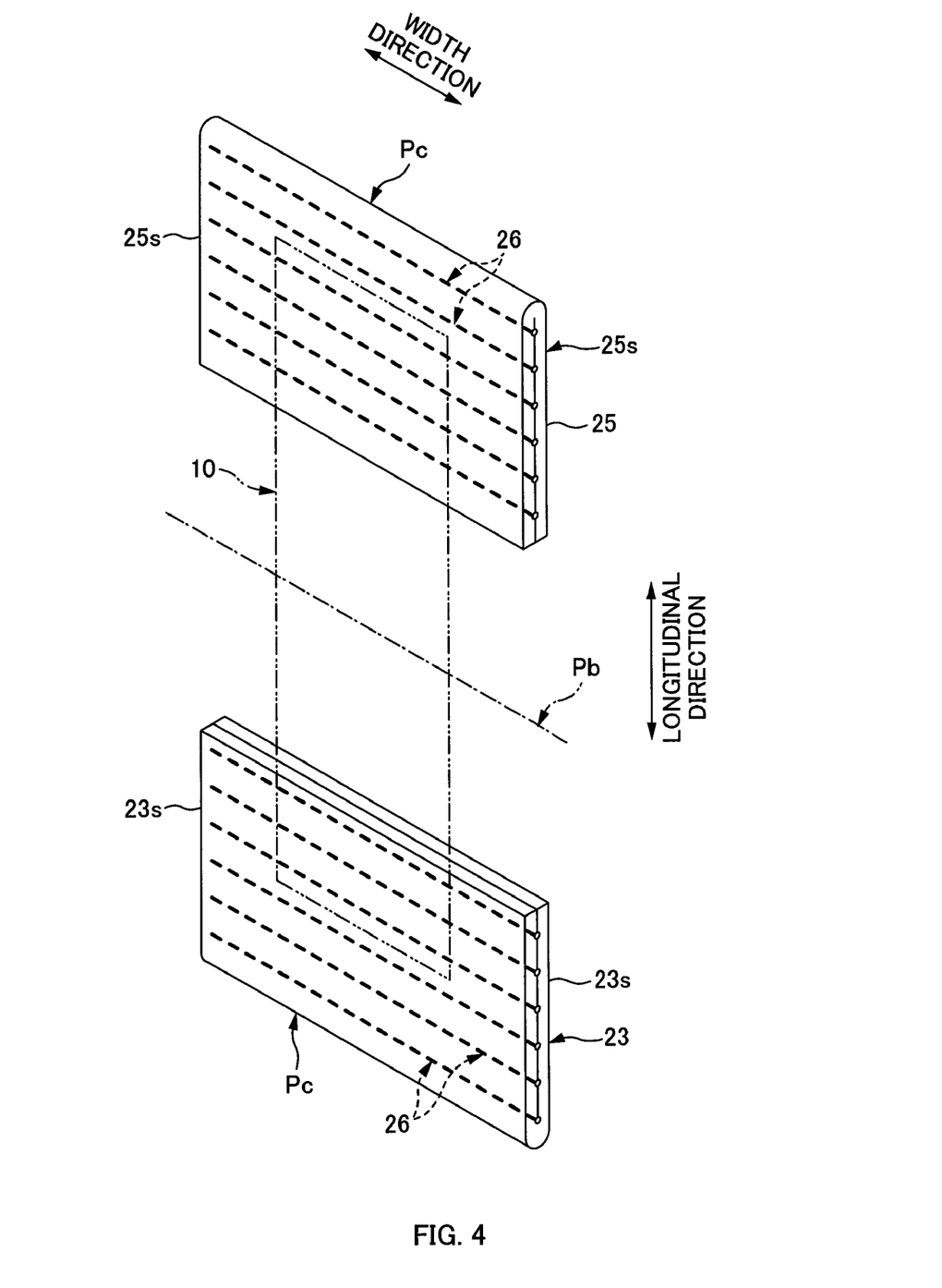
FIG. 4 This is a perspective view for illustrating belt elements 23, 25 of a waist-belt section 20.

As shown in FIG. 2, the absorbent main body 10 is a substantially rectangle, like a strip, as a whole. This absorbent main body 10, as shown in FIG. 4, includes an absorbent body 11 absorbing bodily fluid such as urine, a surface sheet member 12 covering the absorbent body 11 from a side close to wearer's skin, and a back face sheet member 15 covering the absorbent body 11 from an opposite side in the surface sheet member 12 and serving as an exterior of the diaper 1.

The absorbent body 11 is obtained by shaping pulverized pulp containing superabsorbent polymer, etc. into a substantial shape of sandglass, a center in the longitudinal direction is narrowed, as shown in FIG. 2.

The surface sheet member 12 is a member having two-layer structure, in which a sheet of rectangular tissue paper 13 and a rectangular fluid-permeable nonwoven fabric 14 having a width slightly wider than the tissue paper 13 superpose and are affixed to each other with hot-melt adhesive. The absorbent body 11 abuts on and is affixed with hot-melt adhesive to, a surface of the surface sheet member 12 on a side closer to the tissue paper 13. Both end sections of the surface sheet member 12 in the width direction are folded toward a side closer to the absorbent body 11, and thereby both end sections of the absorbent body 11 in the width direction are covered throughout longitudinal direction.

The back face sheet member 15 is, for example, a member having two-layer structure, in which a rectangular fluid-impermeable leakage-proof sheet 16 made of polyethylene, etc., and a rectangular nonwoven fabric 17 having a width slightly wider than this leakage-proof sheet 16 superpose and are affixed to each other with hot-melt adhesive. The absorbent body 11 abuts on and is affixed with hot-melt adhesive to, a surface of the back face sheet member 15 on a side closer to the leakage-proof sheet 16. In addition thereto, both end sections of the back face sheet member 15 in the width direction are folded toward a side closer to the absorbent body 11, and the both end sections 15s, 15s cover the both end sections of the surface sheet member 12 in the width direction throughout the longitudinal direction and are affixed to the surface sheet member 12 with hot-melt adhesive. Thereby, the absorbent body 11 is held by the back face sheet member 15 and the surface sheet member 12 with being sandwiched between these sheet members 15, 12.

Rubber threads 18, 19 respectively adhere to and are fixed on the end sections 15s, 15s in the width direction and folding-line portions 15p, 15p of the back face sheet member 15, along the longitudinal direction with stretching. Therefore, on each of the leg openings 5, 5 of the diaper 1, a pair of around-leg gather sections are formed inside and outside in the width direction.

<<<Waist-Belt Section 20>>>

FIG. 4 is a perspective view for illustrating the belt elements 23, 25 of the waist-belt section 20, and indicates an external shape line of the absorbent main body 10 with double-dotted chained line.

As shown in FIGS. 1, 2, and 4, the waist-belt section 20 includes the belt element 23 that is on the front face side and covers a side close to wearer's abdomen, and the belt element 25 that is on the back face side and covers a side close to wearer's back. These belt elements 23, 25 are welded and joined at each of left and right sections 23s, 25s where wearer's sides abut, so that the belt elements 23, 25 are connected in a ring, to form the waist-belt section 20 as shown in FIG. 1.

As shown in FIG. 4, all of belt elements 23, 25 are made of a rectangular nonwoven fabric, and a strip-like element that is folded in two using a center of the nonwoven fabric in the width direction as a folding position Pc and welded with superposing. Between the surfaces that superpose, a plurality of rubber threads 26 are welded and fixed with stretching along a longitudinal direction of each of the belt elements 23, 25 (the width direction of the diaper 1). This gives these belt elements 23, 25 stretching properties in its longitudinal direction, that is, in the width direction of the diaper 1.

===Manufacturing Equipment 30 of Wearing Article 1===

Figure 5A:
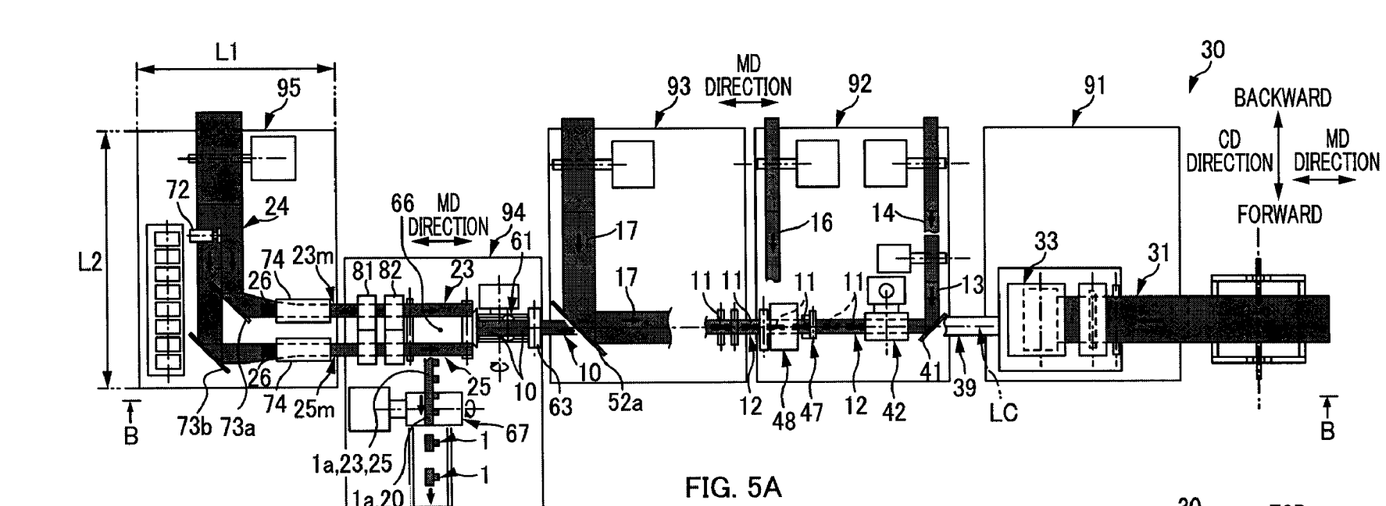
Figure 5B:
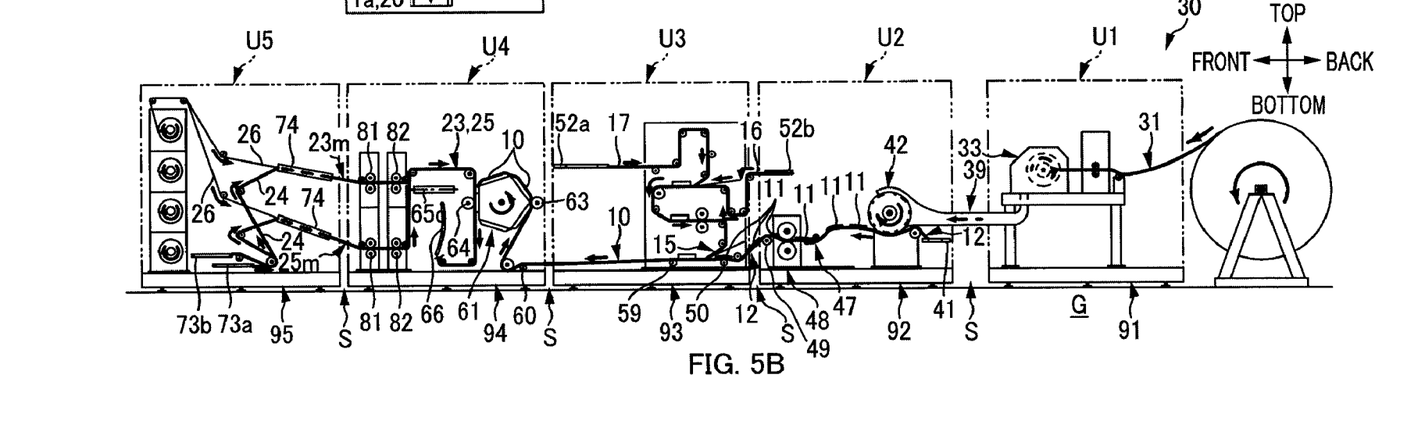

FIGS. 5A and 5B are layouts of the manufacturing equipment 30 of the diaper 1 as the wearing article 1. FIG. 5A shows its plan view, and FIG. 5B shows a view taken along line B-B in FIG. 5A as viewed from the arrow side. Hereinafter, as shown in FIG. 5A, a width direction of the manufacturing equipment 30 is referred to as a CD direction, a direction perpendicular to the CD direction is referred to as an MD direction. Here, as shown in FIG. 5B, the MD direction means any direction in a plane defined by an up-and-down direction and a fore-and-aft direction that is horizontal and perpendicular to the CD direction; that is, the fore-and-aft direction and the up-and-down direction are each one of the MD directions. Also, regardless of the MD direction or the CD direction, there are cases in which expressions upstream and downstream are used for a direction in which a half-completed product of the diaper 1, such as the surface sheet member 12 and the back face sheet member 15, flows.

Incidentally, in the CD direction, a line center LC is set that indicates a reference position of the manufacturing equipment 30 in the width direction. The half-completed products of the diaper 1 mainly flows downstream in the MD direction on the line center LC, and are processed during the processes, to be completed products of the diaper 1.

As shown in FIGS. 5A and 5B, this manufacturing equipment 30 produces the above-mentioned diaper 1, from raw material to finished product, using a sheet member such as a nonwoven fabric and a pulp sheet as a material, and includes five units U1, U2, U3, U4, and U5.

In these units U1, U2, . . . U5, the following eight processes are performed: a first process in which pulverized pulp is shaped into the absorbent body 11; a second process in which the absorbent body 11 is sandwiched between the surface sheet member 12 and the back face sheet member 15, and a continuous body of the absorbent main body 10 is formed; a third process in which at least a part of the belt elements 23, constituting the waist-belt section 20 are produced; a fourth process in which the continuous body of the absorbent main body 10 is severed and the absorbent main body 10 is produced; a fifth process in which the pair of belt elements 23, 25 is affixed to both end sections 10a, 10b of the absorbent main body 10; a sixth process in which the absorbent main body 10 is folded in two and the pair of belt elements 23, 25 superpose; a seventh process in which the superposing belt elements 23, 25 are joined at intervals at a to-be-joined portion and the waist-belt section 20 is produced; and an eighth process in which severing is performed corresponding to the to-be-joined portion at every waist-belt section 20 to form the diaper 1. The first process is performed in the unit U2, the second process is performed in the unit U3, the third process is performed in the unit U5, and the remaining fourth process to the eighth process are performed in the unit U4.

More specifically, as the above-mentioned five units U1, U2, . . . U5, the manufacturing equipment 30 includes: (1) a pulverized-pulp-producing unit U1 that pulverizes a pulp sheet 31 and produces pulverized pulp; (2) an absorbent-body-shaping unit U2 that shapes the pulverized pulp into the absorbent body 11, and places the absorbent body 11 at a certain pitch in the MD direction on the surface sheet member 12 (corresponding to a first sheet member) that continues in the MD direction (corresponding to a flow direction), (3) an absorbent-main-body-forming unit U3 that causes the back face sheet member 15 (corresponding to a second sheet member) that continues in the MD direction and the surface sheet member 12 on which the absorbent body 11 is placed to superpose, and forms the continuous body of the absorbent main body 10 that continues in the MD direction; (4) a joining unit U4 that finishes the diaper 1 by joining the absorbent main body 10 obtained by severing the continuous body of the absorbent main body 10 into product units and the belt elements 23, 25 of the waist-belt section 20 obtained by processing the intermediate products 23m, 25m mentioned below; and (5) an intermediate-product-producing unit U5 that produces the intermediate products 23m, 25m of the belt elements 23, 25 using a nonwoven fabric 24 (corresponding to a third sheet member) as a material, and transports to the joining unit U4 the intermediate products 23m, 25m that is in a state of a continuous body along the MD direction.

With this manufacturing equipment 30, it is possible to reduce the accuracy requirement of the position adjustment between these units. Since it is possible to reduce a time for adjusting positions between units at a time of the construction, a construction time can be shortened. The details thereof are described as follows.

The surface sheet member 12 on which the absorbent body 11 shaped by the absorbent-body-shaping unit U2 is placed is extended from absorbent-body-shaping unit U2 to the absorbent-main-body-forming unit U3 and transferred to the absorbent-main-body-forming unit U3. Accordingly, even if there is some mismatch of a position adjustment between these units U2, U3 in constructing the manufacturing equipment 30, it will not cause a serious problem because the mismatch is absorbed due to flexible deformation of the surface sheet member 12.

In a similar manner, the absorbent main body 10 formed by the absorbent-main-body-forming unit U3 is in a state of a continuous body along the MD direction, and is extended from the absorbent-main-body-forming unit U3 to the joining unit U4 and transferred to the joining unit U4. Accordingly, even if there is some mismatch of a position adjustment between these units U3, U4 in constructing the manufacturing equipment 30, it will not cause a serious problem because the mismatch is absorbed due to flexible deformation of the continuous body of the absorbent main body 10.

In a similar manner, the intermediate products 23m, 25m produced by the intermediate-product-producing unit U5 is in a state of a continuous body along the MD direction, and is extended from the intermediate-product-producing unit U5 to the joining unit U4 and transferred to the joining unit U4. Accordingly, even if there is some mismatch of a position adjustment between these units U5, U4 in constructing the manufacturing equipment 30, it will not cause a serious problem because the mismatch is absorbed due to flexible deformation of the continuous body of the intermediate products 23m, 25m.

Incidentally, the units U1, U2, . . . U5 have their respective rectangular base plates 91, 92, 93, 94, 95 (corresponding to a plate member). Each of the base plates 91, 92, . . . 95 is, for example, prepared by horizontally placing a steel rectangular plate across a frame that is formed by assembling a plurality of shaped steels on a horizontal plane. On a flat, level top surface of each of the base plates 91, 92, . . . 95, devices of each of the units U1, U2, . . . U5 associated with the base plate are placed and fixed. It is possible to move the devices in an integrated manner on a unit basis. A three-dimensional size of each of the units U1, U2, . . . U5 is set to a size that a container according to the JIS or ISO standard can accommodate.

Accordingly, at a time of the construction, each of the units U1, U2, . . . U5 can be moved in an integrated manner on a unit basis and can be accommodated in a container as it is. Therefore, it is possible to transport the units with containers on a unit basis. In addition, when the units U1, U2, . . . U5 are transported with containers, and are each set in a factory place in the destination, the first to eighth processes performed by the units U1, U2, . . . U5 can be performed immediately, without assembling devices in the units and performing the position adjustment. Therefore, it is possible to shorten a construction time for constructing the manufacturing equipment 30.

The details are as follows. When constructing the manufacturing equipment 30, first, the equipment is substantially completed on a unit basis in advance in a dedicated machine factory. The equipment is accommodated in containers on a unit basis and transported to a factory place in the destination. In the destination, the units U1, U2, . . . U5 are each set in the factory place, and thereafter, the position adjustment between the units, and the like is performed. Thus, the manufacturing equipment 30 can substantially be completed. In other words, the assembly of devices in the units and the position adjustment has already been completed in the above-mentioned dedicated machine factory, and therefore the position adjustment between the units is almost all that is required in the factory place. As a result, it is possible to greatly reduce a construction time in the factory place. The units themselves can efficiently be assembled in a dedicated machine factory with dedicated tools, etc. before being transported by containers. Therefore, it is possible to greatly reduce a total construction time for the manufacturing equipment 30.

The above-mentioned container according to the JIS or ISO standard means a container prescribed under 21610 or 21614 of JIS (Japanese Industrial Standards), or ISO (International Organization for Standardization). In the present embodiment, each of units U1, U2, . . . U5 is formed with a length in the fore-and-aft direction of 2100 mm, a height of 2200 mm, and a length in the CD direction of 2750 to 4100 mm. Thus, as a container, a so-called 40 feet, high cube container (whose height is higher than that of a common dry container) is used that can accommodate these units U1, U2, . . . U5. More specifically, a container is used whose interior dimensions of the container are 2350 mm wide, 2685 mm high, and 12020 mm long, and whose door-opening dimensions are 2340 mm wide×2580 mm high; or a container is used whose interior dimensions are 2352 mm wide, 2691 mm high, and 12033 mm long, and whose door-opening dimensions are 2340 mm wide×2577 mm high.

Incidentally, as shown in FIG. 5A, a planar size of each of the units U1, U2, . . . U5 is set in such a manner as a length L1 of a fore-and-aft direction (corresponding to the first direction), in which the half-completed product of the diaper 1 is transferred between the units is shorter than a length L2 in the CD direction (corresponding to the second direction) perpendicular to the fore-and-aft direction. This is for the following purpose: to secure wide spaces in the CD direction for arranging devices, materials, and the like in the units, and simultaneously to shorten a total length of the manufacturing equipment 30 of the diaper 1 in the fore-and-aft direction in which the half-completed product of the diaper 1 is transferred between the units. As a result thereof, positions of the devices provided in the unit U1 to the unit U5 become closer to each other in the fore-and-aft direction, and this increases the relative positioning accuracy of these devices as a whole.

Therefore, it is possible to increase the transferring accuracy of the half-completed product of the manufacturing equipment 30 as a whole; thereby, the diaper 1 can be processed more accurately. Note that the above-mentioned half-completed product of the diaper 1 means the surface sheet member 12, the continuous body of the absorbent main body 10, the intermediate products 23m, 25m of the belt elements 23, 25, or the like.

Incidentally, it is acceptable that, at a time of the construction, when units U1, U2, . . . U5 are placed on a foundation G of the factory place, the units U1, U2, . . . U5 are each installed and fixed on the foundation G with an anchoring member such as an anchor bolt and thereby positional relationship after the position adjustment is maintained in the long term. However, in the present embodiment, a connecting member (not shown) connects, in sequence, units adjacent to each other in the fore-and-aft direction so as to maintain the positional relationship after the position adjustment. More specifically, the connecting member is a member that is made of a shaped steel, for example, and that is inserted into a gap S between the base plates (see FIG. 5B) in order to connect base plates adjacent in the fore-and-aft direction. Both end sections of the connecting member in the fore-and-aft direction are fixed onto the base plate by screwing and the like. While not shown in FIGS. 5A and 5B, the connecting members are provided on each of a gap S between the base plate 91 and the base plate 92, a gap S between the base plate 92 and the base plate 93, a gap S between the base plate 93 and the base plate 94, and a gap S between the base plate 94 and the base plate 95. Here, it is preferable that a plurality of the connecting members are provided lining in the CD direction. With this configuration, it is possible to inhibit a twist that is caused between adjacent base plates and whose axis is in the fore-and-aft direction. After being connected and integrated by the connecting member, the units U1, U2, . . . U5 become in a state in which they cannot individually move. However, as a matter of course, if the connecting member is removed, the units U1, U2, . . . U5 become back to a state in which they can move on a unit basis.

Since the manufacturing equipment 30 completed in this manner allows the height of a processing position of each of units U1, U2, . . . U5 to be positioned lower, the processing accuracy of the unit can be increased. The details are as follows. Generally, to increase positioning accuracy of objects positioned in a low place is easier than in a high place. In this example, on the above-mentioned base plates 91, 92, 95, devices of the units U1, U2, . . . U5 in which the respective base plates are included are directly placed and fixed. Accordingly, the processing position (pass-line) of each of the devices can be positioned lower without using unnecessary legs, etc. at a portion positioned lower than the processing position (pass-line). As a result, it becomes possible to increase the processing accuracy of each of the devices.

Further, since devices can be directly placed on top faces of the base plates 91, 92, 95, it is possible to prevent deterioration of the processing accuracy of the devices, the deterioration being likely to occur when the devices is supported by a so-called panel board. More specifically, in this panel board system, the panel board stands upright vertically and is provided on a foundation. The panel board supports the devices at their own one end on a vertical plane of the panel board. However, in this system, weights of the devices make the panel board curve considerably, and it is difficult to maintain the positioning accuracy of the devices. As a result, the processing accuracy of the devices deteriorates. In this regard, if devices are placed on the top faces of the level base plates 91, 92, 95 according to the present embodiment, it is possible to inhibit deformation of the base plates 91, 92, 95, and to prevent deterioration of the processing accuracy of the devices by increasing the positioning accuracy of the devices.

The units U1, U2, . . . U5 are described below.

(1) Pulverized-Pulp-Producing Unit U1

On the base plate 91 of the pulverized-pulp-producing unit U1, a pulverizer 33 is placed and fixed. The pulverizer 33 pulverizes the pulp sheet 31 and produces pulverized pulp. The pulverized pulp is supplied to a layering drum 42 of the absorbent-body-shaping unit U2, which is described later, through a pulp supplying duct 39. Besides, in the pulp supplying duct 39, a supplying apparatus of superabsorbent polymer (not shown) is provided, and the superabsorbent polymer is mixed while pulverized pulp is passing through the pulp supplying duct 39.

(2) Absorbent-Body-Shaping Unit U2

The absorbent-body-shaping unit U2 produces the surface sheet member 12. On the surface sheet member 12, the absorbent-body-shaping unit U2 places the absorbent body 11 made of pulverized pulp and the like.

Figure 6A:
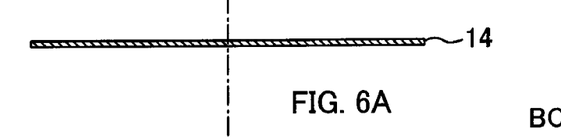
Figure 6B:
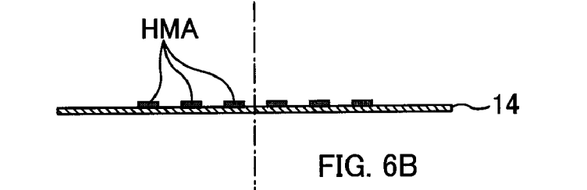
Figure 6C:
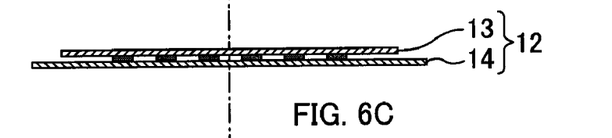

The nonwoven fabric 14 and the tissue paper 13 that are materials of the surface sheet member 12 is sent from backward in the CD direction in the form of a continuous sheet. At this stage, hot-melt adhesive (hereinafter referred to as HMA) is applied to the nonwoven fabric 14 (FIG. 6B). Thus, the nonwoven fabric 14 and the tissue paper 13 superpose and are affixed to each other (FIG. 6C), and the surface sheet member 12 is produced.

Figure 6D:
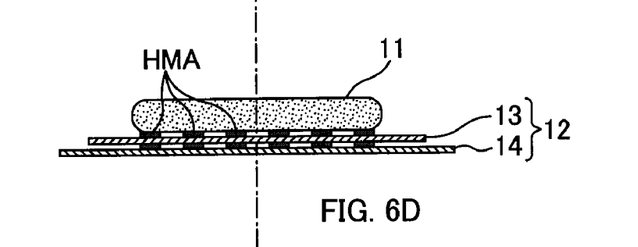
Figure 6E:
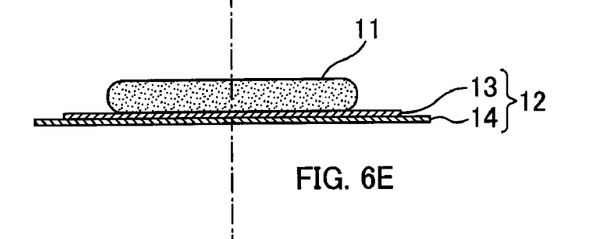

The pulverized pulp and superabsorbent polymer supplied from the pulp supplying duct 39 are layered into a certain shape by the layering drum 42 placed on the base plate 92; thereby the absorbent body 11 is shaped. The absorbent body 11 is placed at a certain pitch in the MD direction, on the surface sheet member 12 whose direction to flow is changed to the MD direction by a turn roller 41 (FIG. 6D). Before placing the absorbent body 11 in this manner, HMA is applied to the surface sheet member 12 (FIG. 6D), which prevents shifting caused in the transportation of the absorbent body 11.

Figure 6F:
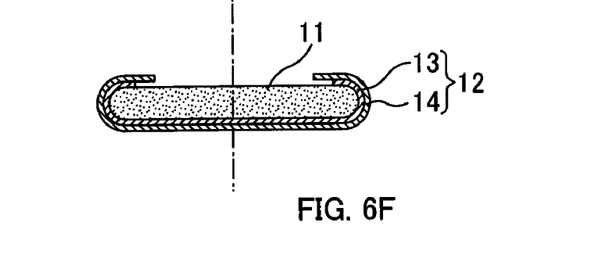

Regarding the surface sheet member 12 on which the absorbent body 11 is placed, both end sections of the surface sheet member 12 in the width direction are folded toward the absorbent body 11 by a guiding member 47 that is placed and fixed on the base plate 92. The surface sheet member 12 is rolled in the C shape in such a manner as to cover the both end sections of the absorbent body 11 in the width direction (FIG. 6F). While the surface sheet member 12 being rolled in the C shape, the absorbent body 11 is pressed down by a pressing roller 48 that is placed and fixed on the base plate 92, to stabilize the shape of the absorbent body 11.

The surface sheet member 12 in which the absorbent body 11 is stabilized is extended between the units U2, U3 by a guide roller 49 located on a most downstream side of the absorbent-body-shaping unit U2 and a guide roller 50 located on a most upstream side of the absorbent-main-body-forming unit U3 to be described later, and is transported to the absorbent-main-body-forming unit U3. In the portion extended between these units U2, U3, weights of the absorbent body 11 and the surface sheet member 12 are supported by only tension of the surface sheet member 12.

(3) Absorbent-Main-Body-Forming Unit U3

The absorbent-main-body-forming unit U3 not only produces the back face sheet member 15, but also forms the continuous body of the absorbent main body 10 by sandwiching the absorbent body 11 between the surface sheet member 12 from the absorbent-body-shaping unit U2 and the back face sheet member 15 and joining them together.

Figure 7A:
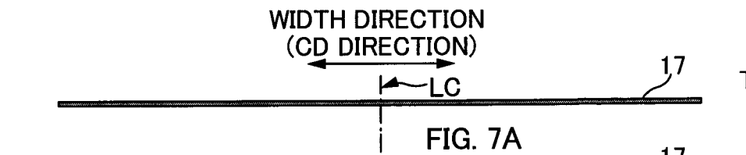
Figure 7B:
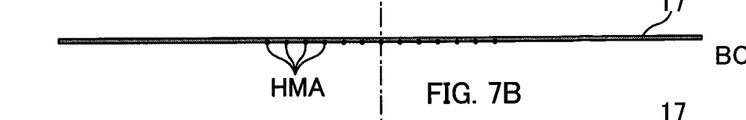
Figure 7C:
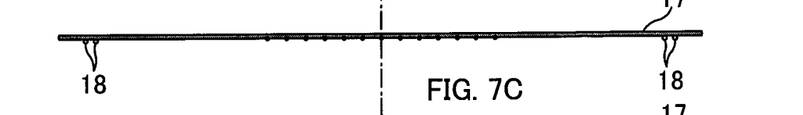
Figure 7D:
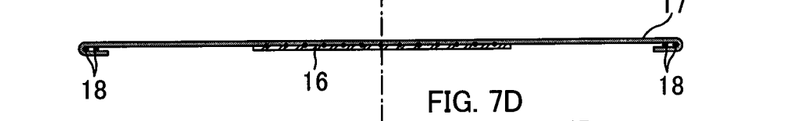
Figure 7E:
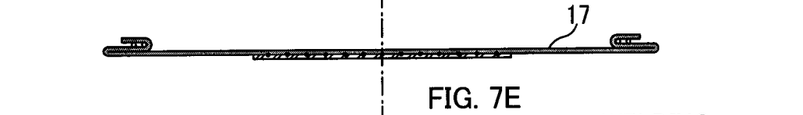
Figure 7F:
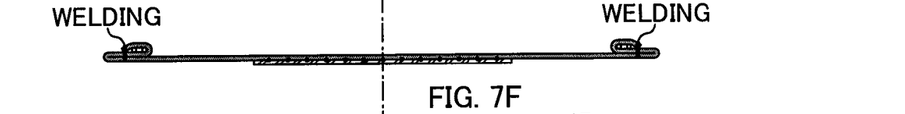
Figure 7G:
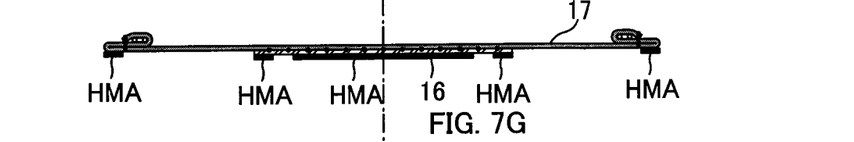
Figure 7H:
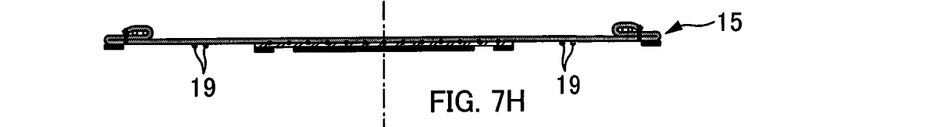

The nonwoven fabric 17 and leakage-proof sheet 16 whose directions to flow are changed to the MD direction by turn rollers 52a, 52b superpose and adhere to each other with HMA between the superposing surfaces, to become a main body of the back face sheet member 15 (FIGS. 7B to 7D). At positions for processing set in a transportation route of the main body, the main body undergoes the following processes: a process in which a rubber thread 18 that is necessary for an inside around-leg gather section in the width direction are welded and fixed, and a process in which both end sections of the main body in the width direction is folded. Thus, the inside around-leg gather section is formed (FIGS. 7C to 7G). Also, a rubber thread 19 that is necessary for an outside around-leg gather section in the width direction is fixed with HMA (FIG. 7H), and as a result, the back face sheet member 15 is completed.

Figure 7I:
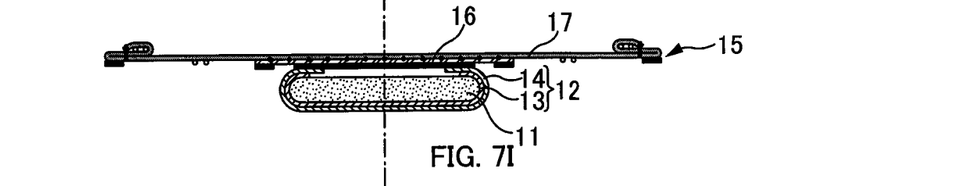
Figure 7J:
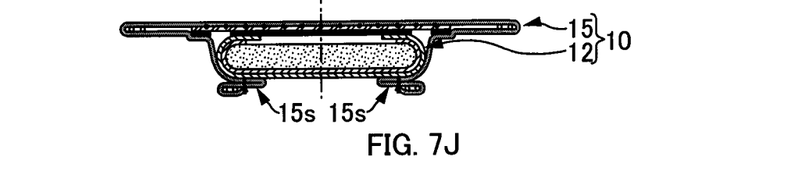

Thereafter, a surface of the back face sheet member 15 on a side closer to the leakage-proof sheet 16 and a surface, on a side closer to the absorbent body 11, of the surface sheet member 12 transported from the absorbent-body-shaping unit U2 superpose, and these surfaces adhere to each other with HMA (FIG. 7I). Further, the both end sections of the back face sheet member 15 in the width direction are folded toward the surface sheet member 12 (FIG. 7J), and are affixed in such a manner as to keep the both end sections folded with HMA applied to the surface sheet member 15 (FIG. 7J). Accordingly, the absorbent main body 10 is formed that is continuous in the MD direction.

The continuous body of the absorbent main body 10 is extended between the units U3, U4 by a guide roller 59 located on a most downstream side of the absorbent-main-body-forming unit U3 and a guide roller 60 located on a most upstream side of the joining unit U4 to be described later, and is transported to the joining unit U4. In the portion extended between these units U3, U4, a weight of the continuous body of the absorbent main body 10 is supported by only its tension.

(4) Joining Unit U4

On the base plate 94 of the joining unit U4, a joining apparatus 61, a two-folding guiding member 66, and a sealing apparatus 67 are placed and fixed.

The joining apparatus 61 causes the continuous body of the absorbent main body 10 transferred from the absorbent-main-body-forming unit U3, to stick to an outer circumferential face of a pentagonal rotating drum 61. During transportation of the continuous body of the absorbent main body 10 by the rotation of the rotating drum 61, the joining apparatus 61 severs the continuous body of the absorbent main body 10 into the absorbent main body 10, with a cutter roll 63 positioned opposite the outer circumferential face. The orientation of the severed absorbent main body 10 is turned 90°, and the both end sections 10a, 10b that has been newly formed by the severing is set in the CD direction. In addition, the continuous body of the belt elements 23, 25 of the waist-belt section 20 transferred from the intermediate-product-producing unit U5 to be described later is respectively pressed to and joined with the both end sections 10a, 10b by a pair of pressure rollers 64, 64 lined up in the CD direction. Thus, a joined body 1a that is substantially in a ladder-like shape is produced.

The two-folding guiding member 66 is a rod extending vertically for example, and curves more backward at an upper portion thereof. The two-folding guiding member 66 abuts a middle portion of the both end sections 10a, 10b of the absorbent main body 10 in the joined body 1a, so that the substantially ladder-like joined body 1a flowing upward in the MD direction is folded in two at the middle portion, and the belt elements 23, 25 superpose. Thus, the direction to flow of the two-folded joined body 1a is changed by a turn roller 65c to forward in the CD direction and the joined body 1a flows.

In the sealing apparatus 67, the two-folded joined body 1a that is moving forward in the CD direction is wrapped around an outer circumferential face of the circular rotating drum 67. In addition, in the sealing apparatus 67, during transportation of the joined body 1a by rotation of this rotating drum 67, the belt elements 23, 25 that oppose and superpose in the joined body 1a are welded and joined at the to-be-joined portion where the waist-belt section 20 abuts wearer's sides. Thereby the waist-belt section 20 that is connected in a ring is formed. A cutter roll (not shown) is arranged opposing the outer circumferential face of the rotating drum 67. This cutter roll severs the waist-belt section 20 at between a pair of the welded-and-joined sections in the to-be-joined portion, into product units of the diaper 1.

(5) Intermediate-Product-Producing Unit U5

The intermediate-product-producing unit U5 produces the intermediate products 23m, 25m of the belt elements 23, 25 using the nonwoven fabric 24 as a material, and transports to the joining unit U4 the intermediate products 23m, 25m that is in a state of a continuous body along the MD direction.

The nonwoven fabric 24 is unwound from backward in the CD direction, and is slit into two by a slitter 72 that is placed and fixed on the base plate 95. After the direction to flow of these two nonwoven fabrics 24, 24 is changed to the MD direction by turn rollers 73a, 73b, a plurality of rubber threads 26 are placed with stretching along the MD direction. Thereafter, the nonwoven fabrics 24, 24 are each folded in two by a two-folding guiding member 74 placed and fixed on the base plate 95. Accordingly, the nonwoven fabrics 24, 24 each become in two layers having the rubber threads 26 therebetween.

This nonwoven fabrics in two layers are each the intermediate products 23m, 25m of the belt elements 23, 25 respectively. These two intermediate products 23m, 25m are respectively supported by the two-folding guiding member 74 at a rearmost position of the intermediate-product-producing unit U5 and the first heat sealing roller 81 at a frontmost position of the joining unit U4, so that the intermediate products 23m, 25m are extended between these units U5, U4 and transported to the joining unit U4. In the portion extended between these units U5, U4, weights of the intermediate products 23m, 25m are supported by only their respective tension.

The two intermediate products 23m, 25m transferred to the joining unit U4 in this manner are respectively welded through a gap between a pair of the vertically arranged first heat sealing rollers 81, and a gap between a pair of vertically arranged second heat sealing rollers 82, the rollers being placed and fixed on the base plate 94 of the joining unit U4. Thus, the rubber threads 26 are affixed to the nonwoven fabric 24, and the intermediate products 23m, 25m become the above-mentioned continuous bodies of the belt elements 23, 25. These two belt elements 23, 25 are transferred to the above-mentioned joining apparatus 61, and joined to the absorbent main body 10.

Other Embodiments

Above, the embodiments of the invention are described. However, the invention is not limited to the embodiments, and the following variations are possible.

In the above-mentioned embodiments, the base plates 91, 92, . . . 95 are illustrated as a base that can move on a unit basis, but the invention is not limited thereto. For example, a frame that is formed by assembling shaped steels, etc. in a rectangular parallelepiped is also acceptable.

In the above-mentioned embodiments, the five units U1, U2, . . . U5 are provided, but the number of units is not limited thereto. For example, it is also acceptable that another unit U6 is provided between the joining unit U4 and the intermediate-product-producing unit U5, and that the intermediate products 23m, 25m transported from the intermediate-product-producing unit U5 is further processed to add a component thereto and sent to the joining unit U4.

The invention claimed is:

1. Equipment for manufacturing a wearing article including an absorbent main body and a waist-belt section, the absorbent main body having an absorbent body for absorbing fluid, said equipment comprising:
    a plurality of units movably arranged on a unit basis for transferring a half-completed product of the wearing article along a first direction, and
    connecting members each of which is arranged between two adjacent units and connects the two adjacent units, wherein
    each of the units has a planar size in which a length in a second direction perpendicular to the first direction is longer than in the first direction,
    each of the units has a height and the lengths of the first direction and the second direction within a size range so that the unit is accommodable in a container according to the JIS or ISO standard,
    the plurality of units is configured to perform at least one of the steps of:
        shaping pulverized pulp into the absorbent body,
        sandwiching the absorbent body between a first sheet member and a second sheet member to define a continuous body of the absorbent main body,
        producing at least a part of a belt element constituting the waist-belt section,
        severing the continuous body of the absorbent main body to obtain the individual absorbent main body,
        affixing a pair of the belt elements to both end sections of the absorbent main body,
        folding the absorbent main body in two, and superposing the pair of belt elements on each others,
        joining the superposed belt elements at intervals at a to-be-joined portion thereof to obtain the waist-belt section, and
        severing the continuous body of the absorbent main body corresponding to the to-be-joined portion for each waist-belt section to obtain the wearing article,
    each of the units has a device and a plate member fixed to the device and supporting the from below, and
    each of the connecting members has end portions directly fixed to the adjacent plate members of the corresponding units.

2. The equipment according to claim 1, wherein the plurality of the units is configured to continuously transport the half-completed product of the wearing article which continuously extend between at least one pair of the units.

3. The equipment according to claim 1, wherein the plurality of units comprises
    an absorbent-main-body-forming unit configured to join the first sheet member on which a plurality of the absorbent bodies is placed along the first direction and the second sheet member continuously extending in the first direction, and to obtain the continuous body of the absorbent main body continuously extending in the first direction, and a joining unit configured to join the belt element constituting the waist-belt section and the absorbent main body, wherein
the continuous body of the absorbent main body is adapted to be transferred along the first direction, and
a weight of the continuous body of the absorbent main body between the absorbent-main-body-forming unit and the joining unit is supported only by tension of the continuous body of the absorbent main body.

4. The equipment according to claim 3, wherein the plurality of units further comprises an absorbent-body-shaping unit configured to shape the pulverized pulp into the absorbent body, and to place the absorbent body at a certain pitch in the first direction on the first sheet member continuously extending in the first direction, wherein
the first sheet member on which the absorbent body is placed is adapted to be continuously extended and transferred from the absorbent-body-shaping unit to the absorbent-main-body-forming unit, and
weights of the absorbent body and the first sheet member continuously extending between the absorbent-body-shaping unit and the absorbent-main-body-forming unit are supported only by tension of the first sheet member.

5. The equipment of a wearing article according to claim 4, wherein the plurality of units comprises a pulverized-pulp-producing unit configured to pulverize a pulp sheet to obtain the pulverized pulp at the absorbent-body-shaping unit.

6. The equipment according to claim 3, wherein the plurality of units further comprises an intermediate-product-producing unit configured to produce an intermediate product of the belt element based on a third sheet member, wherein
the intermediate product is adapted to be transferred in a state of a continuous body along the first direction from the intermediate-product-producing unit to the joining unit,
a weight of the intermediate product continuously extending between the intermediate-product-producing unit and the joining unit is supported only by tension of the intermediate product, and
the joining unit is configured to produce the belt element from the intermediate product.

7. The equipment according to claim 6, wherein joining unit is configured to join each of the end sections of the absorbent main body to one of the belt elements, and to sever the continuous body of the absorbent main body into a certain length in the first direction to obtain the individual absorbent main body.

8. The equipment according to claim 1, wherein plate members are spaced away from each other and each of the connecting members is inserted into the space between two adjacent plate members to connect the corresponding units in the first direction.

9. The equipment according to claim 1, wherein some of the connecting members are arranged lining in the second direction between two adjacent units to prevent a twist between the corresponding two adjacent base plates connected in the first direction.

10. The equipment according to claim 1, wherein the plate members are horizontally arranged and the devices of the units are directly fixed only to the horizontal plate members.

* * * * *